(12) United States Patent
Oh

(10) Patent No.: US 8,905,064 B2
(45) Date of Patent: Dec. 9, 2014

(54) FLOW REGULATOR FOR INFUSION PUMP AND METHOD OF MANUFACTURING THE SAME

(76) Inventor: Seik Oh, Trabuco Canyon, CA (US)

(\*) Notice: Subject to any disclaimer, the term of this patent is extended or adjusted under 35 U.S.C. 154(b) by 681 days.

(21) Appl. No.: 13/252,134

(22) Filed: Oct. 3, 2011

(65) Prior Publication Data

US 2013/0081726 A1    Apr. 4, 2013

(51) Int. Cl.
| | | |
|---|---|---|
| *A61M 5/175* | (2006.01) | |
| *G05D 7/01* | (2006.01) | |
| *A61M 5/168* | (2006.01) | |
| *A61M 39/24* | (2006.01) | |

(52) U.S. Cl.
CPC .......... *G05D 7/0113* (2013.01); *A61M 5/16881* (2013.01); *A61M 2039/2413* (2013.01); *A61M 39/24* (2013.01)
USPC .......... 137/501; 137/505.13; 138/43; 138/46; 251/344; 251/345; 604/248

(58) Field of Classification Search
CPC .............. A61M 5/16813; A61M 5/16877; A61M 5/16881; G05D 7/0106; G05D 7/0113; G05D 7/012
USPC .............. 137/495, 497, 500, 501, 504, 505, 137/505.13; 138/43, 46; 251/344, 345, 346; 604/246, 247, 248
See application file for complete search history.

(56) References Cited

U.S. PATENT DOCUMENTS

| | | | |
|---|---|---|---|
| 3,357,448 A | * | 12/1967 | Martin .......................... 137/501 |
| 3,586,036 A | | 6/1971 | Barnes |
| 3,590,861 A | * | 7/1971 | Chittenden et al. ........... 137/501 |
| 3,807,430 A | | 4/1974 | Keller |
| 3,812,876 A | | 5/1974 | Krieter |
| 3,815,636 A | * | 6/1974 | Menzel .......................... 239/542 |
| 3,841,354 A | * | 10/1974 | McDonnell ..................... 138/43 |
| 3,886,968 A | | 6/1975 | Murrell |
| 3,918,481 A | | 11/1975 | Doe et al. |
| 4,043,332 A | | 8/1977 | Metcalf |
| 4,084,612 A | | 4/1978 | Baehr |
| 4,142,523 A | | 3/1979 | Stegeman |
| 4,142,524 A | | 3/1979 | Jassawalla et al. |

(Continued)

OTHER PUBLICATIONS

The 3M IV Flow Regulator, AVI, Inc. 3M Health Care, Jul. 1990, 3 pages, St. Paul, Minnesota.

(Continued)

*Primary Examiner* — William McCalister
(74) *Attorney, Agent, or Firm* — Knobbe Martens Olson & Bear LLP

(57) ABSTRACT

An ambulatory drug infusion system includes a disposable ambulatory infusion pump and a flow regulator for regulating flow of the drug supplied from the disposable ambulatory infusion pump. The flow regulator includes a cylinder assembly of first, second and third cylinders arranged coaxially. The flow regulator includes a continuous spiral or helical liquid-flow channel formed between the first cylinder and the second cylinder fitted into the first cylinder. The regulator includes bypass through-holes in communication with the spiral or helical channel and formed in the second cylinder. The regulator further includes liquid-flow passages formed between the second cylinder and the third cylinder fitted into the second cylinder. The through-holes are in communication with the passages, respectively. One of the passages can be selected to choose a predetermined flow rate. The regulator further includes a diaphragm valve which can regulate fluid communication between the spiral liquid-flow channel and an outlet.

21 Claims, 18 Drawing Sheets

(56) References Cited

U.S. PATENT DOCUMENTS

| | | | |
|---|---|---|---|
| 4,182,368 A | 1/1980 | Hartley | |
| 4,231,386 A | 11/1980 | Braukmann | |
| 4,241,757 A | 12/1980 | Bron | |
| 4,250,914 A | 2/1981 | Ferrentino | |
| 4,343,305 A | 8/1982 | Bron | |
| 4,428,397 A | 1/1984 | Bron | |
| 4,508,140 A | 4/1985 | Harrison | |
| 4,738,665 A * | 4/1988 | Shepard | 604/248 |
| 4,769,012 A | 9/1988 | Quang et al. | |
| 4,776,367 A | 10/1988 | Hilmersson et al. | |
| 4,796,660 A * | 1/1989 | Bron | 137/504 |
| 4,917,687 A * | 4/1990 | O'Boyle | 604/248 |
| 4,925,451 A * | 5/1990 | Amendolia | 604/246 |
| 4,998,556 A * | 3/1991 | Bron | 137/501 |
| D319,506 S * | 8/1991 | Lal et al. | D24/129 |
| 5,101,854 A | 4/1992 | Bron | |
| 5,137,522 A * | 8/1992 | Bron | 604/247 |
| 5,143,116 A | 9/1992 | Skoglund | |
| 5,190,075 A | 3/1993 | Tentler et al. | |
| 5,232,012 A | 8/1993 | Toraason | |
| 5,234,025 A | 8/1993 | Skoglund et al. | |
| 5,280,805 A | 1/1994 | Skoglund | |
| 5,301,713 A | 4/1994 | Skoglund | |
| 5,421,363 A | 6/1995 | Bron | |
| 5,487,405 A | 1/1996 | Skoglund | |
| 5,520,661 A | 5/1996 | Lal et al. | |
| 5,622,204 A | 4/1997 | Skoglund | |
| 5,931,186 A | 8/1999 | Skoglund | |
| 5,941,267 A | 8/1999 | DeLand et al. | |
| 5,983,926 A | 11/1999 | Mastuzawa | |
| 6,056,008 A | 5/2000 | Adams et al. | |
| 6,254,576 B1 | 7/2001 | Shekalim | |
| 6,270,483 B1 | 8/2001 | Yamada et al. | |
| 6,273,117 B1 | 8/2001 | McPhee | |
| 6,598,618 B1 | 7/2003 | Shay | |
| 6,619,308 B2 | 9/2003 | Massengale et al. | |
| 6,679,865 B2 * | 1/2004 | Shekalim | 604/253 |
| 6,805,156 B2 | 10/2004 | Sasao | |
| 6,892,755 B2 | 5/2005 | Black | |
| 6,932,107 B2 | 8/2005 | Kirchner et al. | |
| 6,938,642 B2 | 9/2005 | Massengale et al. | |
| 7,011,651 B2 | 3/2006 | Lee et al. | |
| 7,114,520 B2 | 10/2006 | Massengale et al. | |
| 7,546,846 B2 | 6/2009 | Massengale et al. | |

OTHER PUBLICATIONS

Cousseau, et al., Improved Micro-Flow Regulator for Drug Delivery Systems, Debiotech S.A., pp. 527-530, Lausanne, Switzerland.

* cited by examiner

FLOW REGULATOR FOR INFUSION PUMP AND METHOD OF MANUFACTURING THE SAME

BACKGROUND

1. Field

The present disclosure relates to a flow regulator for an ambulatory infusion pump.

2. Discussion of Related Technology

Ambulatory infusion pumps allow hospital patients to remain mobile without having to carry a pole holding intravenous (IV) therapy devices. There is a growing demand for home IV therapy using disposable ambulatory pumps. Disposable ambulatory pumps, most of which are mechanical ambulatory pumps, have a characteristic flow pattern: the flow-rate is higher at the beginning and decreases throughout the life of infusion due to the decrease in the volume, and therefore pressure, of the drug reservoir. Thus, the precision of flow of disposable infusion pumps is typically in the range of ±15% to ±20%, which is significantly worse than that (±5% to ±8%) of electronic infusion pumps.

The advantages of disposable infusion pumps are their light weight, small size, simplicity of use, independence from an external power supply, elimination of programming errors, low initial cost, quiet operation, and disposability. Disadvantages include the possibility of inaccurate flow rates, fixed reservoir volume, lack of facility to change the flow rate and bolus-dose volume to provide adequate analgesia, inability to trace the history of the analgesia demand by the patient, and long-term cost.

There are several types of disposable infusion pumps, such as elastomeric, positive pressure (spring-powered or gas-pressure-powered), negative pressure (vacuum), and patient control analgesia (PCA) pumps. The accuracy of each pump's flow rate is dependent on several factors, including temperature, fluid viscosity, atmospheric pressure, back pressure, partial filling, and storage. Nonelectric disposable pumps may utilize a mechanical restrictor within the flow path to determine the speed of pressurized fluid. The preset flow rate of each device is mainly determined by the dimensions of the flow restrictor and the pressure supplied by the pressure source, for instance, a stretched elastomeric reservoir. The configuration of the stretched elastomeric reservoir offers the advantages of simplicity and convenience, which has resulted in wide acceptance of the device by the marketplace. However, certain limitations remain; one of them is variability of the flow rate due to changes in the upstream pressure provided by the elastomeric balloon (or other pressure generation means).

The foregoing discussion in this section is to provide general background information, and does not constitute an admission of prior art.

SUMMARY

One aspect of the invention provides a drug infusion flow regulating apparatus. The apparatus may comprise: an inlet configured to receive liquid into the apparatus; an outlet configured to discharge the liquid from the apparatus; a cylinder assembly comprising a first cylinder, a second cylinder and a third cylinder that are arranged substantially coaxially along an axial direction; the first cylinder comprising a first interior surface; a continuous spiral or helical thread formed into the first interior surface of the first cylinder; the second cylinder fitted into the first cylinder and comprising a second interior surface and a second exterior surface; a spiral or helical liquid-flow channel formed between the first cylinder and the second cylinder through the continuous spiral thread, the spiral liquid-flow channel being in fluid communication with the inlet; a plurality of longitudinal grooves extending substantially parallel to the axial direction and formed into the second cylinder on the side of the second interior surface; a plurality of through-holes formed in the second cylinder and in fluid communication with the spiral liquid-flow channel; the third cylinder fitted into the second cylinder and comprising a third exterior surface; a plurality of independent liquid-flow passages formed between the second cylinder and the third cylinder, wherein each of the plurality of independent liquid-flow passages is in fluid communication with the spiral liquid-flow channel via at least one of the plurality of through-holes; and a diaphragm valve configured to regulate fluid communication between the spiral liquid-flow channel and the outlet.

In the foregoing apparatus, two immediately neighboring liquid-flow passages may be liquid-tightly separated from each other by close contact between the second interior surface and the third exterior surface. The apparatus may be configured such that at least one of the plurality of passages is selected to form a fluid channel extending to the diaphragm valve while the other passages do not form a fluid channel extending to the diaphragm valve. The apparatus may further comprise a fourth cylinder received within the third cylinder and rotatable relative to the third cylinder, wherein at least one of the plurality of passages forms a fluid channel extending to the diaphragm valve depending upon a rotational position of the fourth cylinder relative to the third cylinder.

Continuing in the foregoing apparatus, the diaphragm valve may comprise a deformable diaphragm and a valve seat that are received in an interior space of the fourth cylinder, wherein the deformable diaphragm divides the interior space into a first chamber and a second chamber, wherein the inlet is fluidly connected to the first chamber, and the outlet is fluidly connected to the second chamber, wherein the diaphragm is configured to deform toward the valve seat and recover away from the valve seat in response to the pressure differential between the first and second chambers. The deformable diaphragm may be slidable within the fourth cylinder such that the size of the first and second chambers varies. The apparatus may further comprise a stopper configured to stop the movement of the diaphragm at a predetermined location.

Still in the foregoing apparatus, the plurality of through holes may be angularly separated along the second cylinder's circumference. The plurality of independent liquid-flow passages may be angularly separated along the third cylinder's circumference. One or more of the plurality of independent liquid-flow passages may have a liquid-flow passage portion generally extending along the axial direction. The first cylinder is made of a first material, the second cylinder is made of a second material and the third cylinder is made of a third material, wherein the first material may be substantially harder than the second material and the second material may be substantially harder than the third material. The second cylinder may be made of a non-elastomeric material having a modulus of elasticity greater than about 2,000 psi. The third cylinder may be made of an elastomeric material having a modulus of elasticity smaller than about 1,000 psi.

Also in the foregoing apparatus, each of the plurality of longitudinal grooves may extend throughout the length of the second cylinder. The plurality of through-holes may be located at different positions in the axial direction. Two immediately neighboring passages may be liquid-tightly separated by liquid-tight fitting of the third cylinder into the second cylinder. The apparatus may further comprise a fifth cylinder fitted into the third cylinder and located between the third cylinder and fourth cylinder.

Another aspect of the invention provides a method of making the aforementioned apparatus. The method may comprise: providing the first cylinder made of a first material and comprising a continuous spiral or helical thread formed into the first interior surface, the first cylinder having a first diameter measured on the first interior surface; providing the second cylinder made of a second material softer than the first material, the second cylinder having a second diameter on the second exterior surface, wherein the second diameter is greater than the first diameter; and press-fitting the second cylinder into the first cylinder, wherein the second material is a non-elastomer having a modulus of elasticity greater than about 2,000 psi.

In the foregoing method, press-fitting of the second cylinder into the first cylinder causes deformation of the second cylinder along the plurality of grooves such that the second diameter shrinks when press-fitting. The method may further comprise: providing the third cylinder made of a third material that is an elastomer having a modulus of elasticity smaller than about 1,000 psi, wherein the third cylinder comprises a plurality of longitudinal ribs protruding from the third exterior surface; and press-fitting the third cylinder into the second cylinder such that two immediately neighboring passages are liquid-tightly separated by press-fitting of the third cylinder into the second cylinder.

DETAILED DESCRIPTION OF EMBODIMENTS

Figure 1A:
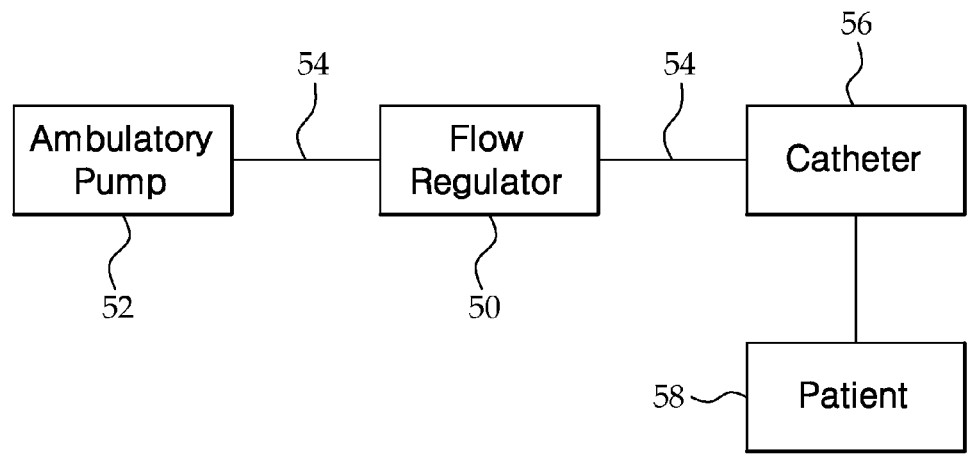
FIG. 1A illustrates an ambulatory infusion system in accordance with one embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

In the following detailed description, terms of orientation such as "upper," "lower," "longitudinal," "horizontal," "vertical," "lateral," "top," "bottom," "middle," and "end" may be used to simplify the description in the context of the illustrated embodiments. Because other orientations are possible, however, the present invention should not be limited to the illustrated orientations.

Ambulatory Drug Infusion System

Figure 1B:
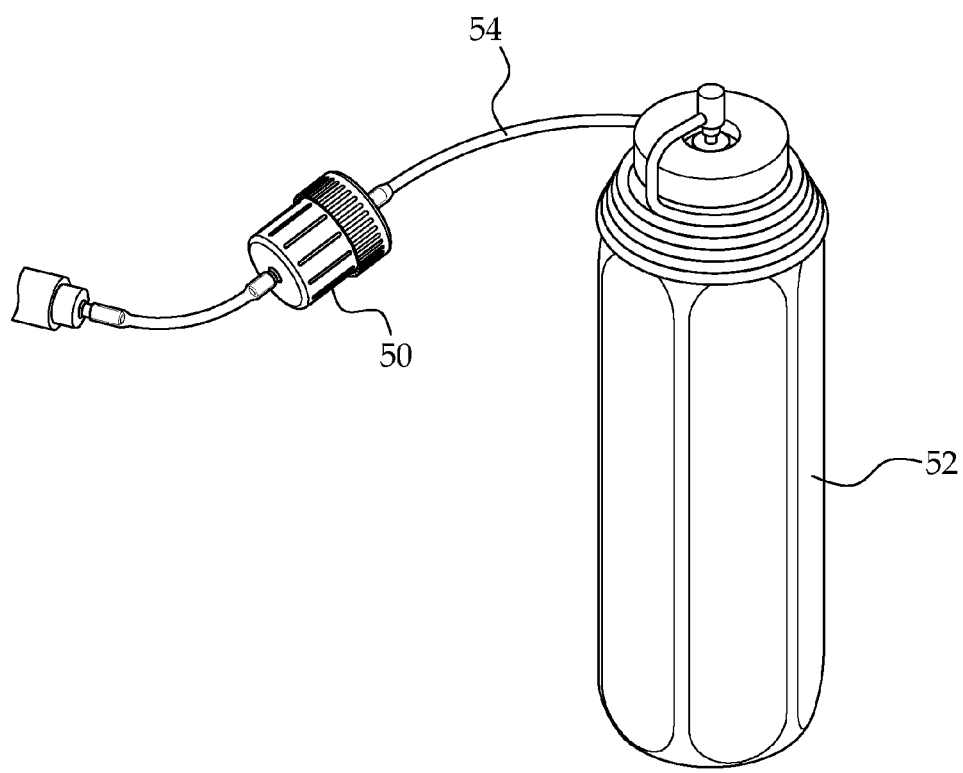
FIG. 1B illustrates an ambulatory infusion system in accordance with another embodiment.

Referring to FIGS. 1A and 1B, in one embodiment, a flow regulator 50 is connected to an ambulatory infusion pump 52 via a tube 54. The tube 54 is connected to a catheter 56 which is installed in the body of a patient 58.

Referring to FIG. 1B, in some embodiments, the flow regulator 50 is connected to an ambulatory infusion pump 52 via a tube 54. The flow regulator 50 can be used with various disposable ambulatory infusion pumps 52, such as an ambulatory, single-use, portable, disposable, infusion device which is designed to deliver solution at a flow rate between about 0.5 ml/h and about 300 ml/h. This configuration offers the advantages of simplicity and convenience, which has resulted in wide acceptance of the platform by the marketplace. However, certain limitations remain; among them is variability in the solution flow rate due to variation in the pressure driving force provided by the elastomeric balloon, mechanical spring or vacuum, and a reduction in flow rate if the device is attached to an additional flow resistance downstream of the capillary (e.g. an indwelling catheter).

The illustrated flow regulator 50 improves the flow rate accuracy of disposable ambulatory infusion pumps. This makes the flow accuracy of the disposable ambulatory infusion pumps competitive with that of electronic pumps. The flow regulator 50 can be attached to any mechanical type infusion pump, creating constant flow characteristics regardless of the change in up-stream pressure. The flow regulator 50 also provides the capability to vary the flow rate during infusion, which is commonly required with pain management. Integration of these improvements into any mechanical type disposable ambulatory infusion pumps would decrease infusion variability and improve patient satisfaction.

In some embodiments, the flow regulator 50 improves flow rate accuracy over the entire infusion period to about +/−8%, rivaling that of a typical electromechanical infusion pump. It also reduces the variability of medication delivery times under standard conditions by eliminating the effects of variability of pressure sources. Furthermore, it minimizes the effect of drug volumetric flow rate to head height, and downstream resistance resulting from different access points or the use of different types of catheters.

Flow Regulator

In some embodiments, like a mechanical system, a mechanical flow regulator 50, as illustrated in FIGS. 1A, 1B, 2A, and 2B, provides a uniform, stable volumetric flow rate for the entire drug infusion period regardless of upstream (supply) pressure variation (about 6 psig to about 12 psig) and minimizes the effect of downstream (back pressure) variation in the range of 0 psig to about 2 psig. Variations in fill volume do not affect the flow rate as long as the minimum supply pressure is maintained.

Components

Figure 2A:
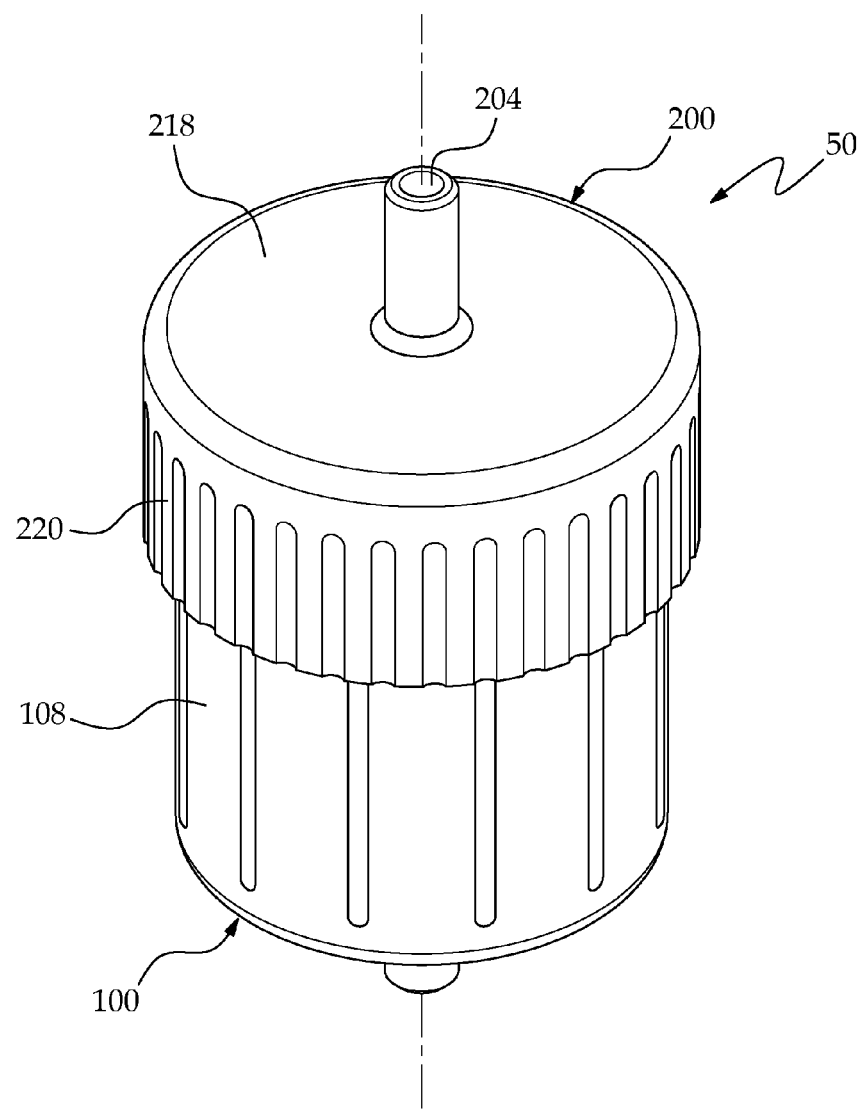
FIG. 2A is a perspective view of a flow regulator in accordance with one embodiment.
Figure 2B:
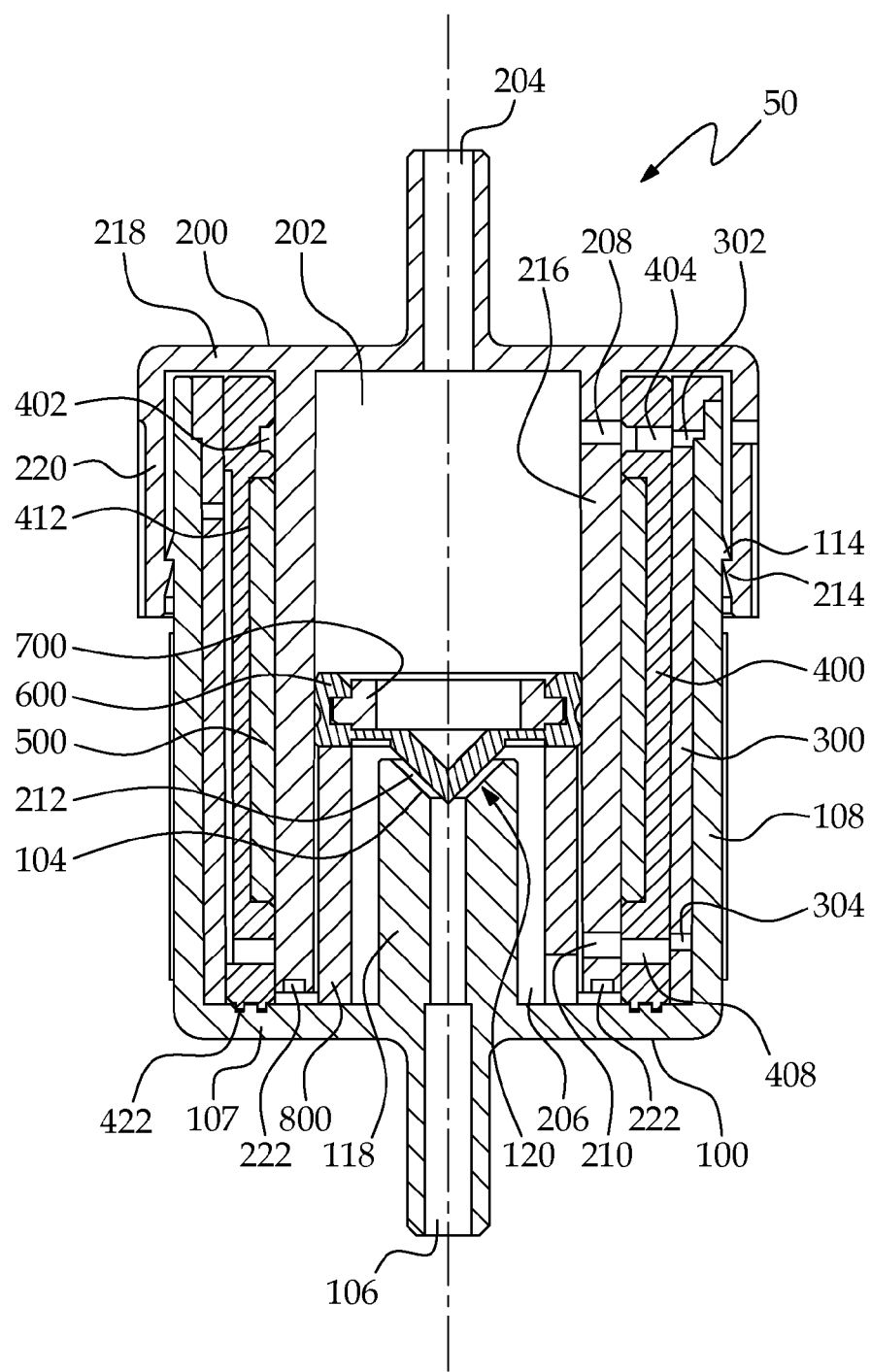
FIG. 2B is a vertical cross-section view of the flow regulator shown in FIG. 2A.
Figure 3:
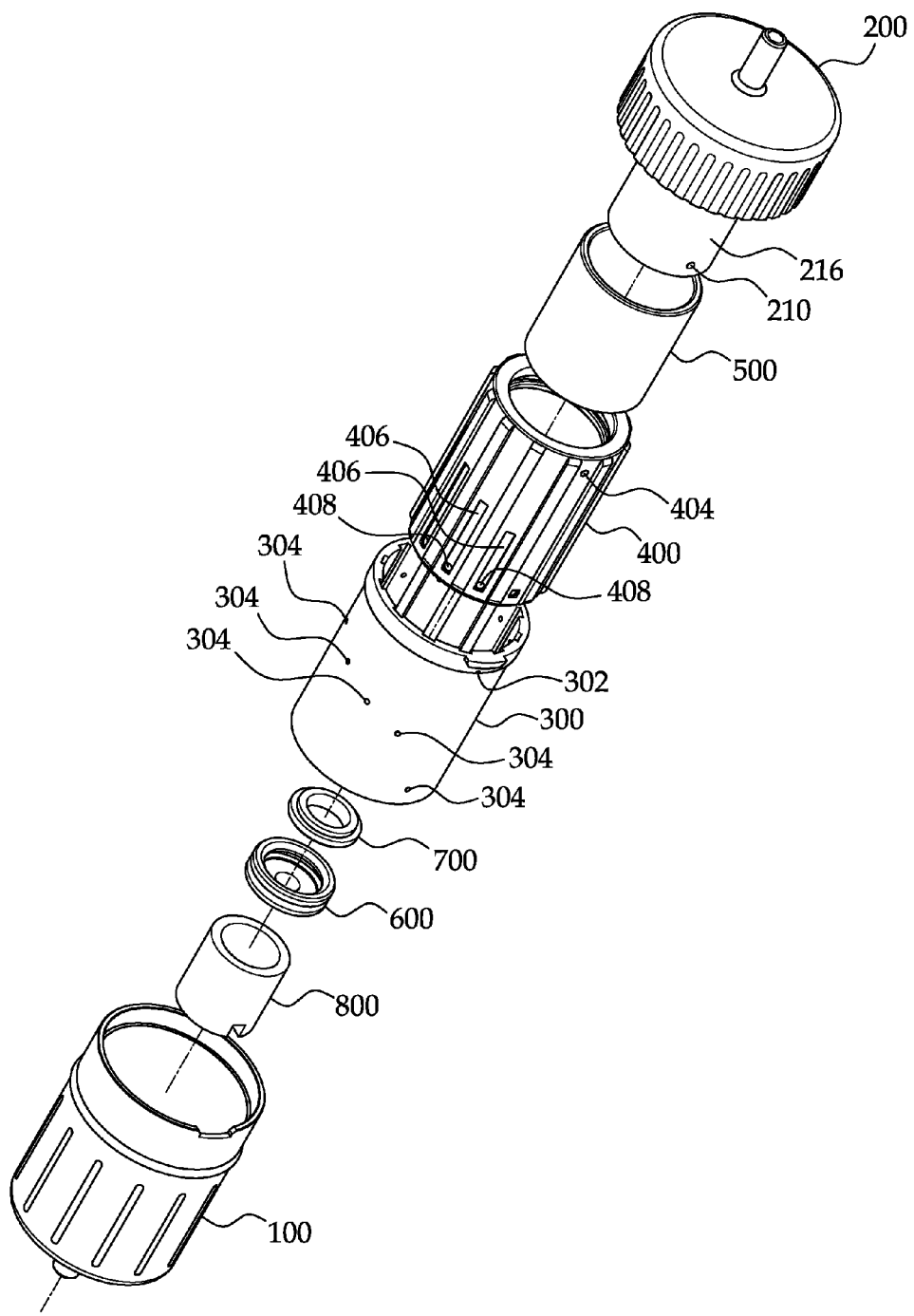
FIG. 3 is an exploded view of the components of the flow regulator shown in FIG. 2A.
Figure 4:
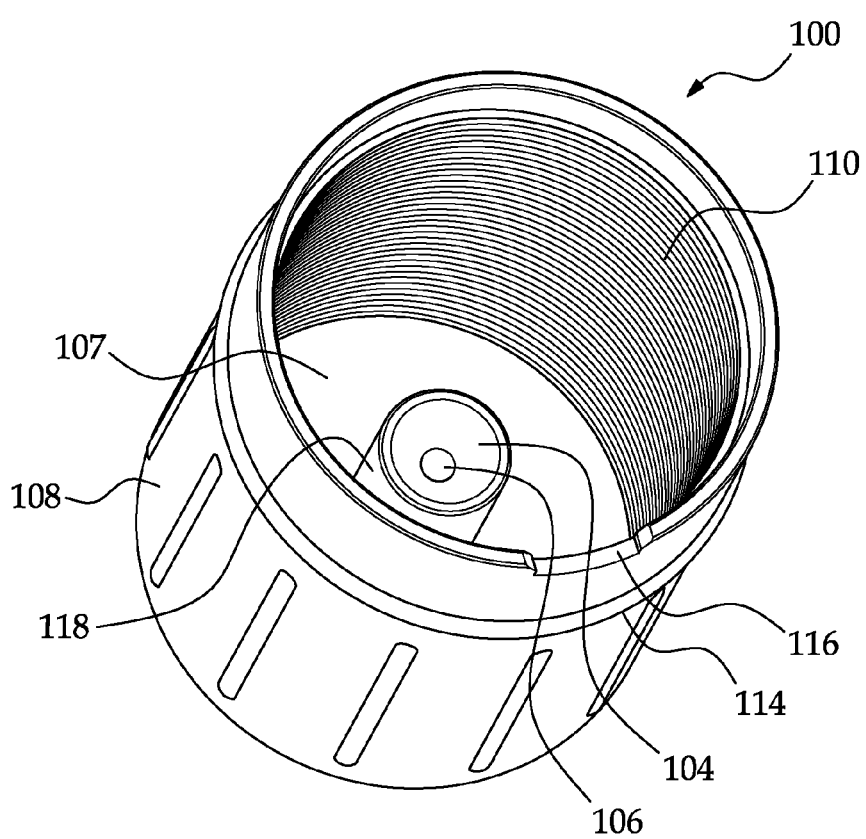
FIG. 4 is a perspective view of a bottom housing of the flow regulator in accordance with one embodiment.
Figure 5:
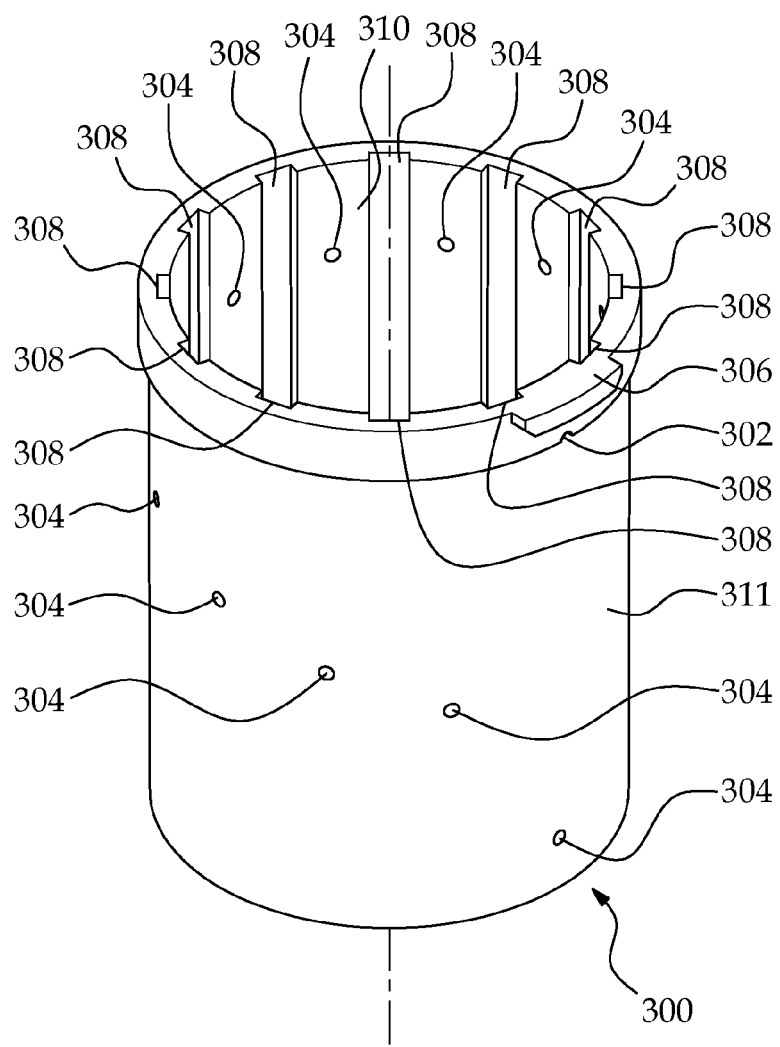
FIG. 5 is a perspective view of a sleeve of the flow regulator in accordance with one embodiment.
Figure 6A:
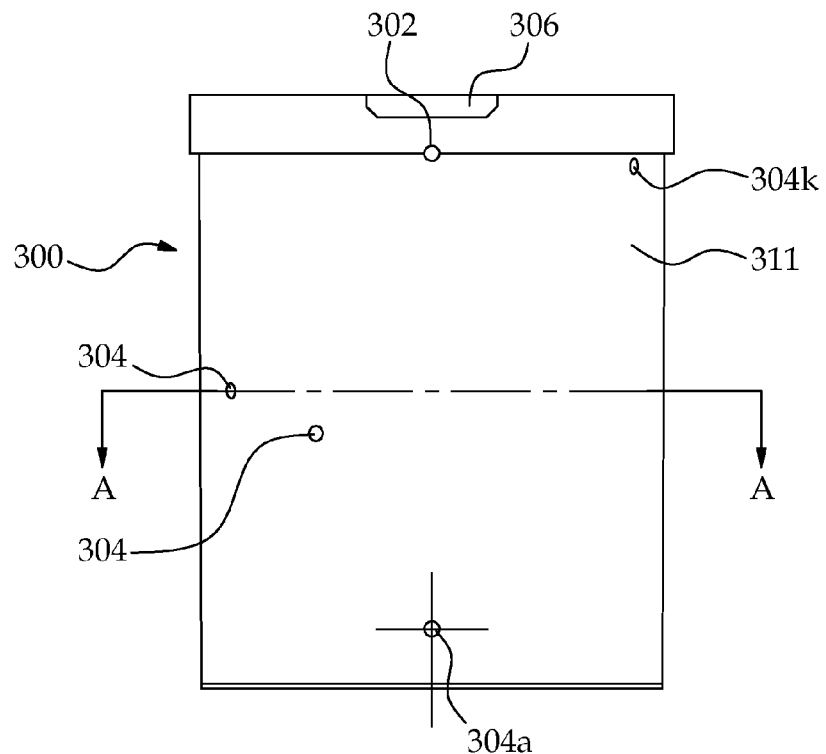
FIG. 6A is a side view of the sleeve shown in FIG. 5.
Figure 6B:
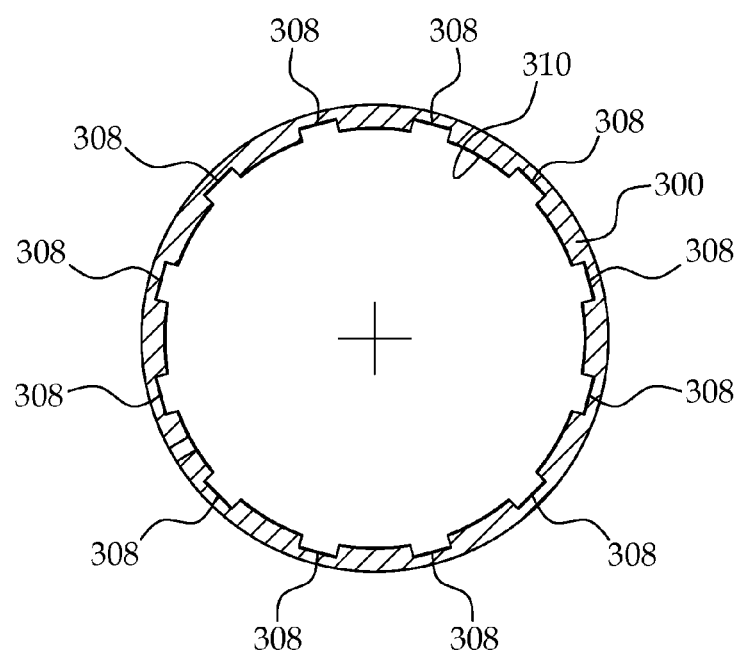
FIG. 6B is a sectional view of the sleeve of FIG. 6A, taken along line A-A.

Referring to FIGS. 2A, 2B and 3, in some embodiments the flow regulator 50 includes a bottom housing 100 and a rotor cap 200 which are engaged with each other and form an enclosure. Ring shaped components including a sleeve 300, a seal liner 400 and a seal liner support 500, are inserted between an outer wall 108 of the bottom housing 100 and a cylindrical wall 216 of the rotor cap 200. A piston 600, a piston ring 700 and a stopper 800 is placed in the cylindrical chamber 216 of the rotor cap 200.

In some embodiments, the flow regulator 50 includes eight plastic components 100, 200, 300, 400, 500, 600, 700 and 800. The components include five thermoplastic parts 100, 200, 300, 500, 700 and three elastomeric parts 400, 600, 800, but not limited thereto. Some components, for example, the bottom housing 100 can be made of a transparent material. In some embodiments, all components are made of biocompatible medical grade plastics, and the assembly procedure is straightforward for manufacturing simplicity.

Overall Fluid Flow

Referring to FIGS. 2B 3, 9, 11, and 13C in some embodiments, the pressurized drug solution fluid flows into an upper inlet chamber 202 of the flow regulator 50 through the inlet port 204. As soon as the fluid fills the inlet chamber 202, the fluid presses the piston 600 downward toward an outlet chamber 206. The fluid also flows from the inlet chamber 202 to the outlet chamber 206 through an upper through-hole 208 of the rotor cap 200. The fluid flows through the upper through-hole 208 into a circumferentially extending groove 402 of the seal liner 400, which is positioned at the same level as the upper-through hole 208 of the inlet chamber 202. The fluid then flows through an upper through-hole 404 of the seal liner 400, followed by an upper through-hole 302 of the sleeve 300. Next, the fluid enters a spiral or helical conduit or channel 102 (see FIG. 7) formed between the bottom housing 100 and the sleeve 300. The fluid then enters a communication through-hole 304 of the sleeve 300 corresponding to a selected preset flow rate, followed by a vertical recess or passages 406 of the seal liner 400 corresponding to a selected preset flow rate. Next, the fluid enters a flow rate selection hole 408 of the seal liner 400 corresponding to a selected preset flow rate, followed by a bottom hole 210 of the rotor cap 200, and into the outlet chamber 206.

The fluid in the outlet chamber 206 flows through a clearance 212 between the piston 600 and a valve seat 104 of the bottom housing 100 and flows out through an outlet port 106 of the bottom housing 100.

Bottom Housing

Referring to FIGS. 2A, 2B, 3, 4, 5, 6A and 7, in some embodiments, the bottom housing 100 includes a bottom wall 107 and a cylindrical outer wall 108 extending from the bottom wall 107. The outer wall 108 includes a spiral or helical thread 110 on its inner surface 112. The outer wall 108 further includes a first protrusion 114 on its outer surface, and the first protrusion 114 forms a snap-fit engagement with a second protrusion 214 of the rotor cap 200. The outer wall 108 includes a key recess 116 on its top portion, and the recess 116 receives and engages with an engaging key 306 of the sleeve 300. This structure can minimize rotation or movement of the sleeve 300 with respect to the bottom housing 100 after being assembled and help alignment of the bottom housing and the sleeve in one predetermined direction.

In some embodiments, the bottom housing 100 includes a central boss 118 extending from the bottom wall 107. At the top of the boss 118, a valve seat 104 is provided. The boss 118 includes an outlet port 106.

Spiral or Helical Conduit

Figure 7:
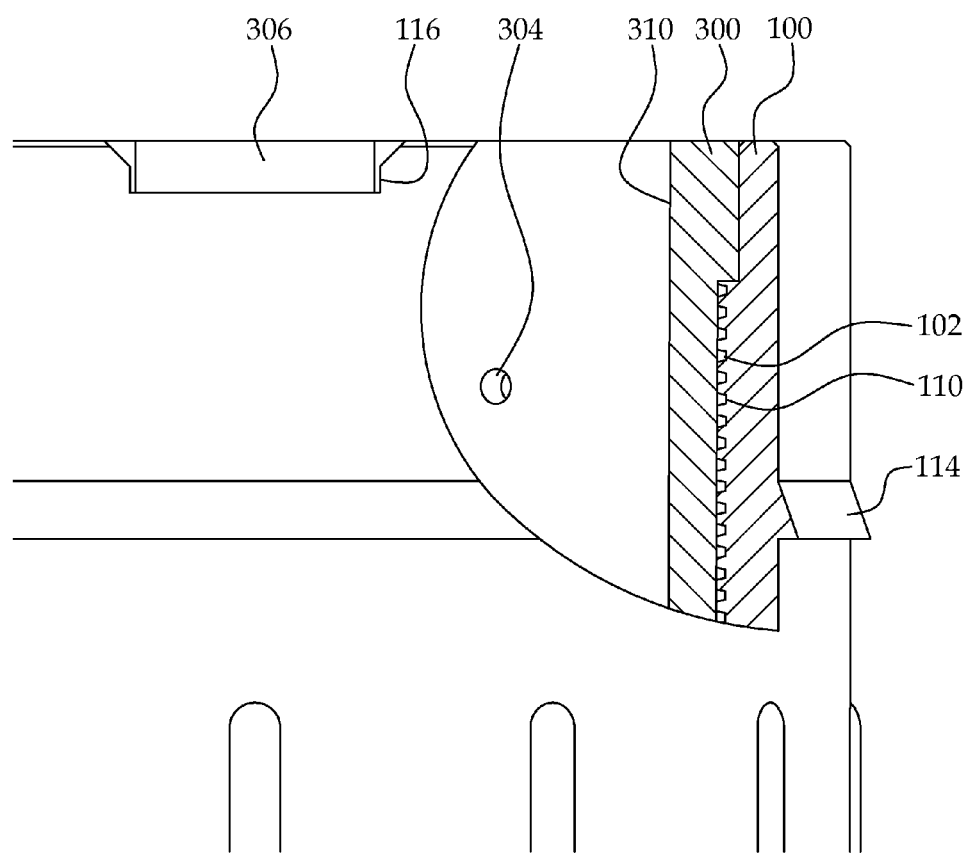
FIG. 7 is a partial side view of a bottom housing and a sleeve engaged with each other in accordance with one embodiment.

Referring to FIGS. 2B, 3, and 7, in some embodiments, once the bottom housing 100 engages with the sleeve 300, the thread 110 forms the spiral or helical conduit or flow-restricting spiral or helical conduit 102. The spiral or helical conduit 102 communicates with the upper chamber (inlet chamber) 202 and the lower chamber (outlet chamber) 206. Specifically, the spiral or helical liquid-flow channel 102 is in fluid communication with an upper through-hole 302 and a plurality of through-holes 304 which determine the flow rate. The fluid can flow from the upper inlet chamber 202 to the lower outlet chamber 206 through the spiral conduit 102.

Specifically, in some embodiments, the fluid solution flows through a long and narrow spiral channel 102 which serves as a flow restrictor. A fine thread 110 is fabricated on the inner surface 112 of the bottom housing 100. The open thread 110 formed in the inner surface 112 of the bottom housing 100 then becomes the closed conduit 102 by inserting the sleeve 300 with an interference fit. In some embodiments, both the length and the cross section of the thread 110 are calculated using the Hagen-Poiseuille equation, taking into account pump pressure, viscosity of solution, and desired flow.

The flow regulator 50 is used with a disposable ambulatory pump. Therefore, it is desirable to size the flow regulator 50 to be comfortable to wear. In some embodiments, the dimensions of the thread channel 102 are determined by considering the overall size of the flow regulator 50. For example, the diameter of the flow regulator 50 is approximately one inch, while the length is approximately one and a half inches. Thus if the lowest flow rate is approximately 1 mL/hr with an average pressure of approximately 8 psi from other disposable ambulatory pumps, then the size of the thread (cross section, pitch and the length) becomes only a few thousandths of an inch.

Spiral or Helical Threads

In some embodiments, the fine thread 110 can be injection-molded as part of the bottom housing 100. A sectional shape of the thread 110 (or conduit 102) is a trapezoid, but not limited thereto, so that it can secure sufficient contact area with the mating sleeve 300 while efficiently delivering fluid volume. In alternative embodiments, a sectional shape of the spiral thread (or conduit) 102 is selected from the group of shapes including semi-circular, triangular, trapezoidal, rectangular and polygonal. In one embodiment, the fine thread 110 has a pitch of a few thousandths of an inch. A trapezoidal or polygonal section of the thread 110 has sides a few thousandths of an inch long.

In some embodiments, when injection-molding, appropriate roundness can be applied to the corner of the trapezoid for easy flow of material, which results in a complete filling in of the fine thread 110. An equivalent diameter of the circular cross section was converted from the cross section of the rounded trapezoid to determine the flow rate under nominal pressure of the infusion pump 52. In some embodiments, the dimension of the thread cross section can be significantly larger than the diameter of the flow restrictor commonly used for infusion pumps. Therefore, the possibility of flow blockage during infusion is minimized.

Compared to the traditional glass capillary or tubing type flow restrictor, the threaded channel 102 involves a long length, which makes it easy to vary the flow rate by simply adjusting the length.

Interference Fit—Thermoplastic Sleeve

With reference to FIGS. 2A-7, in some embodiments, the spiral or helical open thread 110 becomes a closed spiral conduit 102 by inserting the sleeve 300 with an interference fit. The cylinder shaped sleeve 300 is inserted into the thread-formed bottom housing 100 with an interference fit to close the open thread 110, forming the closed conduit 102. The material of the body of the bottom housing 100 in which the thread 110 is formed is harder than the material of the sleeve 300, so the insertion of the sleeve 300 does not damage or deform the fine thread 110. As shown in FIGS. 5, 6A, 6B, and 7, the sleeve 300 includes an interfacing outer surface 311 and inner surface 310 including vertical grooves or notches 308. This structure of grooves 308 can provide the sleeve 300 with deformability and resilience when the sleeve 300 is mechanically press-fit into the bottom housing 100.

In some embodiments, the bottom housing 100 and the sleeve 300 are made of generally rigid and hard plastic materials, but not limited thereto. In some embodiments, the bottom housing 100 is made of a thermoplastic like polycarbonate, and the sleeve 300 is made of a softer thermoplastic material than the housing 100, like a high density polyethylene (HDPE) or a medium density polyethylene (MDPE), but not limited thereto. The thread 110 is not crushed when the sleeve 300 is inserted into the housing 100 with an interference fit, as the bottom housing 100 is more rigid and harder than the sleeve 300.

In some embodiments, the bottom housing 100 is made of a material with a modulus of elasticity between about 250,000 psi and about 450,000 psi. In certain embodiments, the bottom housing material has a modulus of elasticity which may be about 200,000 psi, about 220,000 psi, about 250,000 psi, about 270,000 psi, about 300,000 psi, about 350,000 psi, about 400,000 psi, about 450,000 psi, or about 450,000 psi. In alternative embodiments, the bottom housing material has a modulus of elasticity which may be within a range defined by two of the foregoing values.

In some embodiments, the sleeve 300 is made of a material with a modulus of elasticity between about 50,000 psi and about 150,000 psi. In certain embodiments, the sleeve housing material has a modulus of elasticity which may be about 2,000 psi, about 5,000 psi, about 10,000 psi, about 20,000 psi, about 30,000 psi, about 40,000 psi, about 50,000 psi, about 70,000 psi, about 100,000 psi, about 110,000 psi, about 120,000 psi, about 130,000 psi, about 140,000 psi, about 150,000 psi, about 160,000 psi, or about 180,000 psi. In alternative embodiments, the sleeve material has a modulus of elasticity which may be within a range defined by two of the foregoing values.

In some embodiments, injection-molding may be used for mass production instead of individual machining, but not limited thereto. However, the size of the thread 110 is constrained by the tolerance of the injection-molding and the shrinkage rate of the selected material. If the interference is too tight, it would be very difficult to assemble the two parts, the bottom housing 100 and the sleeve 300. If it is too loose, fluid may leak or shunt between the threads 110.

In the illustrated embodiments, one of the methods of resolving the above mentioned tolerance issue is to make the sleeve 300 to be compressible or resilient. The vertical grooves 308 work as a vertical crack or notch to the sleeve 300, which results in a reduction of the moment of inertia, and consequently a reduction of the stiffness of the sleeve 300, when it is compressed by the interference fit. This allows for more interference between the two bodies, i.e. the bottom housing 100 and the sleeve 300, which can manage the injection-molding tolerances without damaging the thread 110, or causing a fluid leak.

Interference Fit—Elastomeric Sleeve

Figure 8:
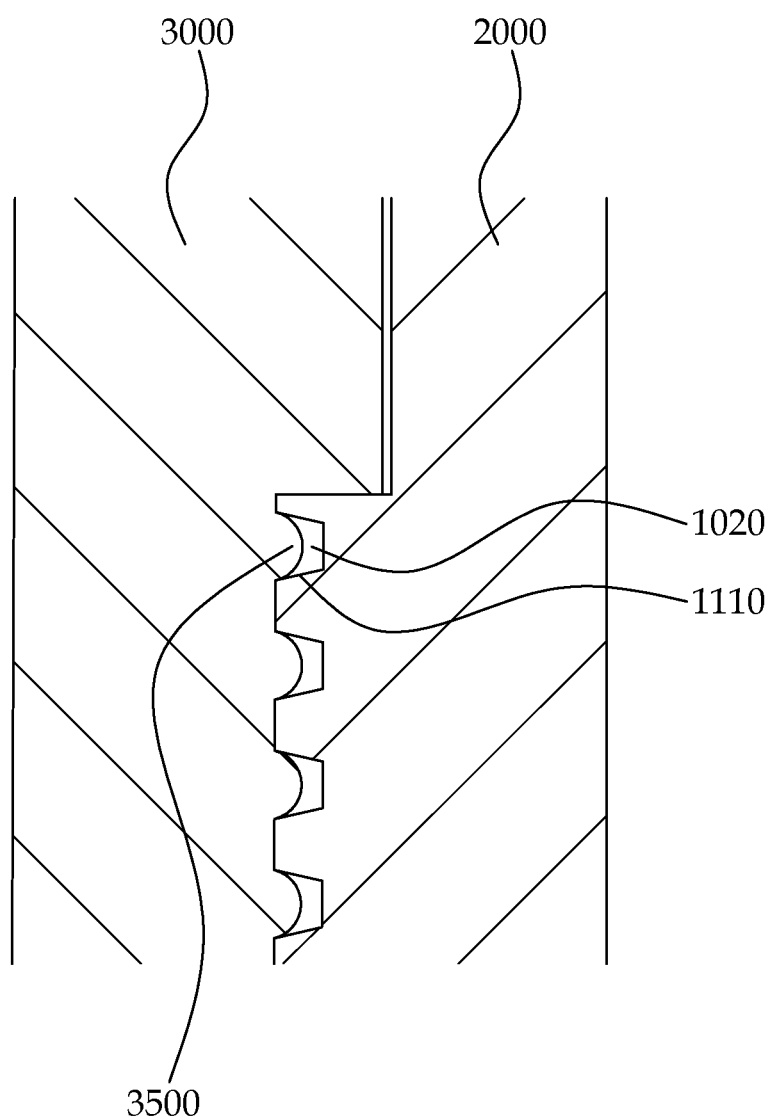
FIG. 8 is a partial sectional view of a bottom housing and a sleeve engaged with each other in accordance with one embodiment.

With reference to FIG. 8, in one example of a flow regulator, an elastomeric sleeve 3000 may be used instead of the rigid sleeve 300 shown in FIG. 7. As shown in FIG. 8, however, when engaged with a bottom housing 2000, the sleeve 3000 can be partially deformed such that deformed portions 3500 of the sleeve 3000 can protrude toward threads 1110 and reduce the size of the section of the closed conduit 1020. This may cause unexpected partial blocking of the conduit 1020 which may differ the flow rate from designed.

Such elastomeric material generally has a Shore A Hardness between about 30 Ha and about 70 Ha. Further, such elastomeric material generally has a modulus of elasticity smaller than about 1,000 psi. In some examples, the elastomeric material has a modulus of elasticity between about 200 psi and about 500 psi. Contrastingly, the sleeve 300 in accordance with the embodiment illustrated in FIG. 7 has a material significantly more rigid and harder than the elastomeric material.

Bypasses from Spiral Conduit

Referring to FIGS. 2-5, 6A, and 11, in some embodiments, once the liquid reaches the upper through-hole 302 of the sleeve 300, it continues to flow through the narrow spiral conduit 102. The sleeve includes several (for example, in the illustrated embodiment, eleven, but not limited thereto) communication through-holes 304 fabricated on the side wall of the sleeve 300. In one embodiment, the plurality of through-holes 304 are located at different positions in the longitudinal direction of the sleeve 300 on the non-grooved outer surfaces 311 and extend through the thickness of the sleeve 300. Using the fact that flow rate is inversely proportional to the length of the fluid path, the location (height) of each of the through-holes 304 is calculated accordingly. For instance, if the inlet upper through-hole 302 is located on the upper most area at the beginning of the spiral conduit 102, then the appropriate through-hole 304a (one of the through-holes 304) for the lowest flow rate (for example, approximately, 1 mL/hr) is located at the very bottom of the spiral conduit 102, thereby using the full length of the conduit 102 for the fluid path. In the illustrated embodiment, for the appropriate through-hole 304k (one of the through-holes 304) for the highest flow rate (for example, approximately, 16 mL/hr) is positioned to use the smallest length of the conduit 102 for the fluid path.

Figure 11:
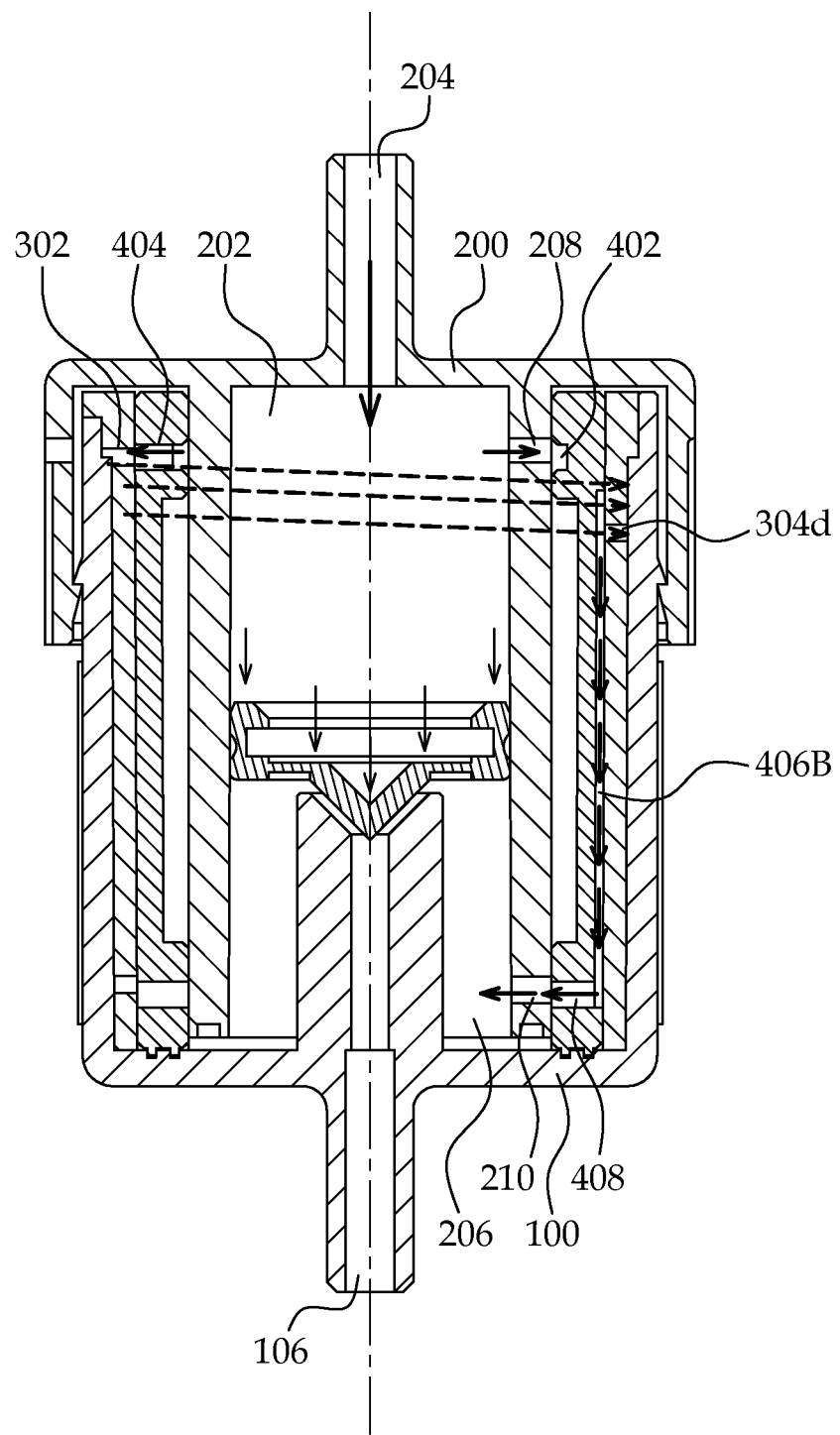
FIG. 11 is a sectional view of a bottom housing, a sleeve, a seal liner and a rotor cap of the flow regulator in accordance with one embodiment.
Figure 12A:
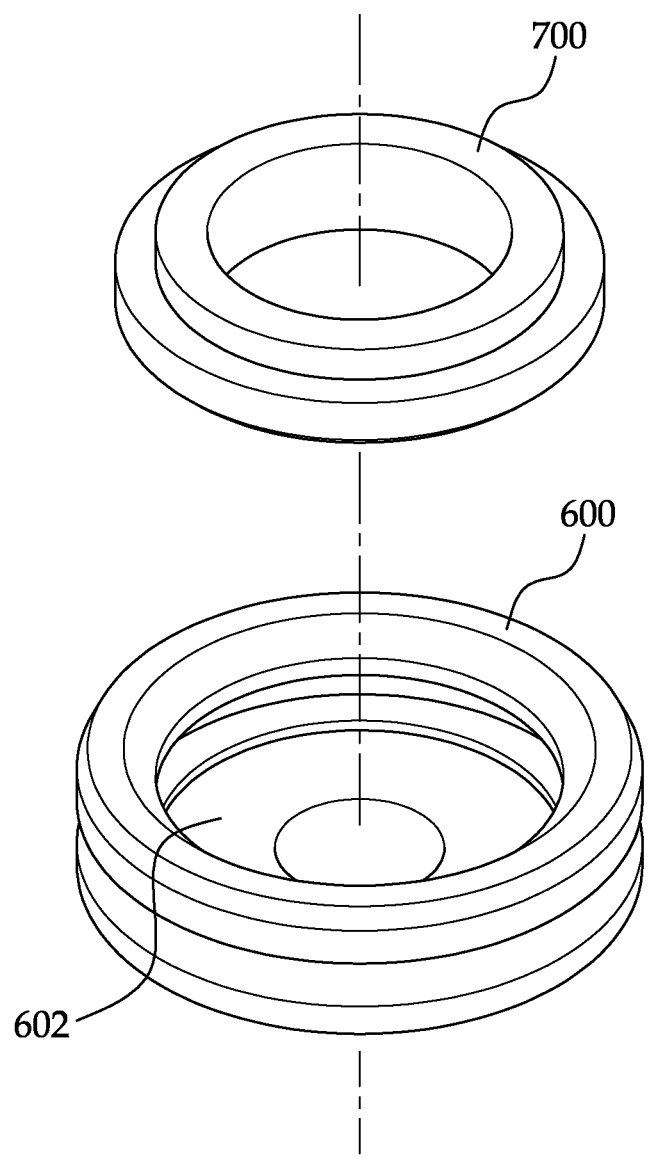
FIG. 12A is an exploded view of a piston assembly of the flow regulator in accordance with one embodiment.
Figure 12B:
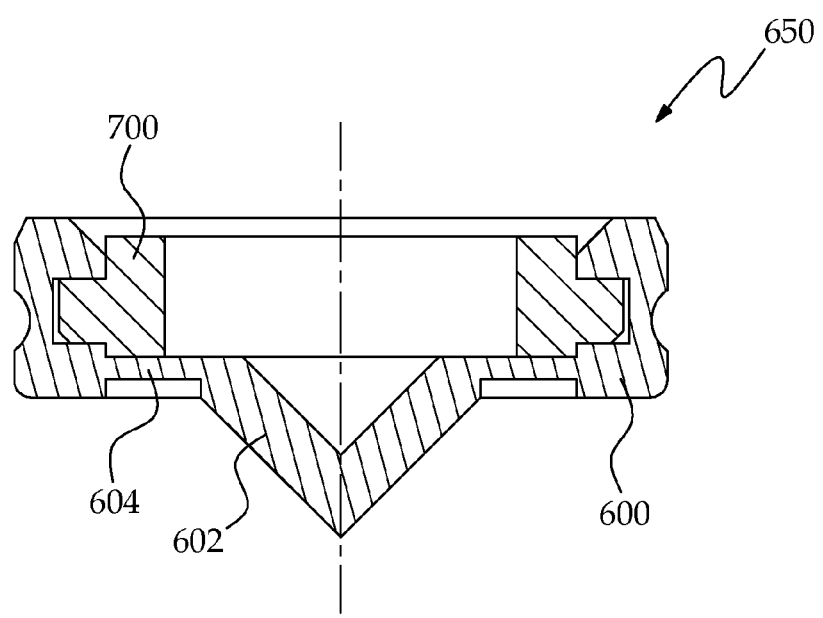
FIG. 12B is a sectional view of the piston assembly in accordance with one embodiment.

Flow rates, in between the lowest option (for example, approximately 1 mL/hr) and the highest option (for example, approximately 16 mL/hr) are attained by dividing length of the channel 102 by the number of desired flow rates, but not limited thereto. Examples of flow rates within this range include, but are not limited to, approximately 1 mL/hr, approximately 2 mL/hr, approximately 3 mL/hr, approximately 4 mL/hr, approximately 5 mL/hr, approximately 6 mL/hr, approximately 7 mL/hr, approximately 8 mL/hr, approximately 10 mL/hr, approximately 12 mL/hr, and 16 mL/hr. For instance, if the desire is to create eleven discrete flow rates from 1 mL/hr to 16 mL/hr, then the necessary length for each flow rate is calculated from the total length of the helical conduit 102. Then, each hole's vertical (or altitude) position is determined. The through-holes 304 are about 30 degrees azimuthally apart, but not limited thereto. Referring to FIG. 11, the fourth through-hole 304d for the fourth flow rate (for example, approximately 4 mL/hr) is located at an altitude between the altitudes of the first and eleventh holes 304a and 304k. (See FIG. 6A.)

Seal Liner

Referring to FIGS. 2A, 2B, 9, 10 and 11, the seal liner 400 is inserted in and engaged with the sleeve 300. In some embodiments, the seal liner 400 is made of an elastomer like silicone or rubber. In certain embodiments, the elastomer of the seal liner generally has a Shore A Hardness between about 30 Ha and about 70 Ha. In some examples, the elastomer of the seal liner generally has a modulus of elasticity smaller than about 1,000 psi.

In some embodiments, the seal liner 400 can be rotatable with respect to the rotor cap 200 while providing a fluid seal. In other words, the seal liner 400 allows the rotor cap 200 to rotate while providing a seal between the two bodies, i.e. the rotor cap 200 and the seal liner 400. At the end of the seal liner 400 a seal 422 is provided. The seal 422 contacts the bottom wall 107 of the bottom housing 100 to provide a fluid seal.

An elastomer is good for providing seals with a generous interference fit. However, the frictional coefficient of an elastomer is high, which may result in difficulties in turning the rotor cap with the interfacing seal liner 400. In some embodiments, an indentation 412 is made inside of the seal liner 400, reducing the contact area between the rotor cap 200 and the seal liner 400, and thus, minimizing the frictional resistance. Thus, the contact area between a cylindrical wall 216 of the rotor cap 200 and the seal liner 400 is minimized by creating an indentation to reduce the frictional resistance.

Ribs and Grooves

Figure 10:
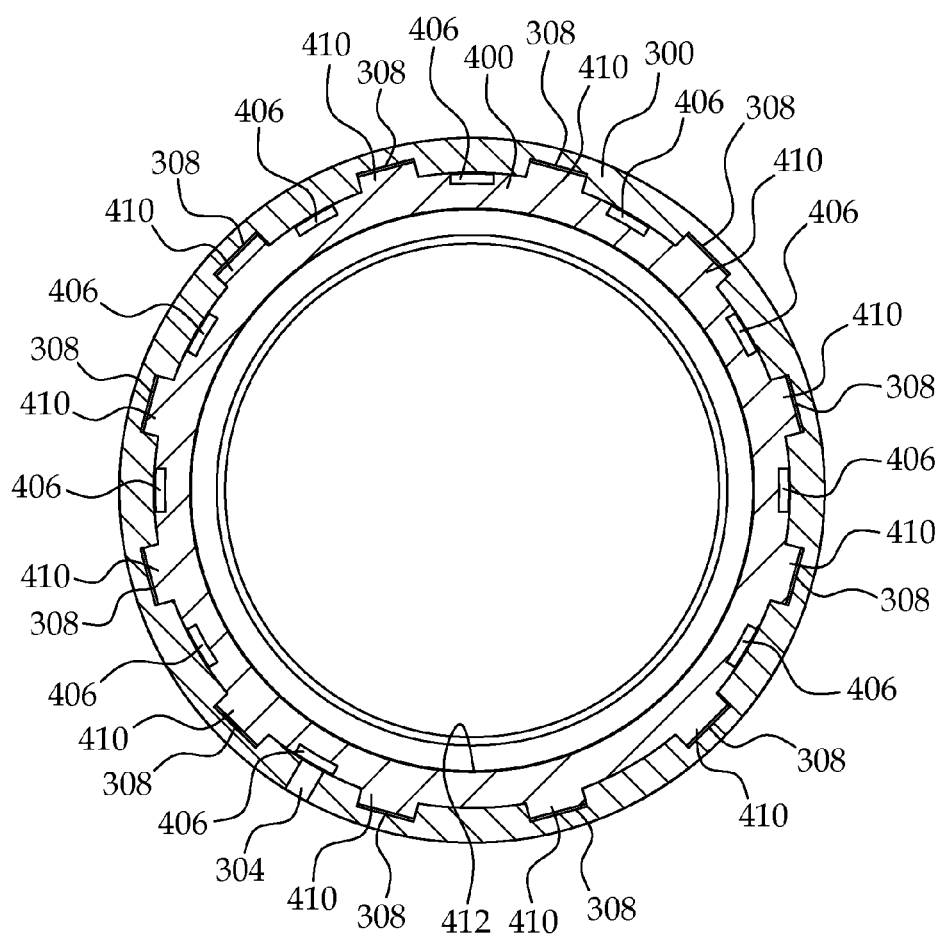
FIG. 10 is a sectional view of a sleeve and a seal liner which are engaged with each other.

In some embodiments, the outer surface of the seal liner 400 liquid-tightly contacts the sleeve 300, so it can provide a fluid seal between the seal liner 400 and the sleeve 300, except at the communicating holes 304 of the sleeve 300. The outer surface of the seal liner 400, in some embodiments, includes the vertical ribs 410, each of which can be inserted in and engaged with one of the vertical grooves 308 of the sleeve 300. As shown in FIG. 10, the vertical grooves 308 of the sleeve 300 receive the mating vertical ribs 410 of the seal liner 400. In other words, the vertical ribs 410 (in the illustrated embodiments, twelve vertical ribs 410) of the seal liner 400 align and engage with the mating vertical grooves 308 of the sleeve 300 so as to inhibit the seal liner 400 from rotating with respect to the sleeve 300. Thus, this configuration inhibits the seal liner 400 from rotating along with the rotor cap 200. As such, the seal liner 400 is fixed to the mating sleeve 300 by interlocking vertical ribs 410 and mating vertical grooves 308. In the illustrated embodiment, the outer surface of the seal liner 400, other than the vertical ribs 410, is the seal area with the interfacing sleeve 300. The seal liner support 500 pushes the seal liner 400 towards the sleeve 300, which provides a fluid seal, except at the vertical fluid-flow recesses or passages 406 of the seal liner 400. The vertical passages 406 are made in the outer surface, each creating a fluid path, but not limited thereto. The length of each of the grooves 406 can match one of the through-holes 304 of the sleeve 300. In alternative embodiments, these fluid communication grooves or passages 406 can be made the inside surface of the sleeve 300 rather than the outside surface of the seal liner 400.

Vertical Liquid-Flow Passages

Referring to FIGS. 2A, 2B, 3, 5, 6A, 9, 10 and 11, in some embodiments, each of the through-holes 304 fluidly communicates with one of the vertical grooves 406 fabricated on the interfacing surface of the mating seal liner 400. The size of the holes 304 and the vertical grooves 406 are relatively large compared to the size of the section of the closed conduit 102 (thread 110). Thus, when the fluid reaches the highest hole 304k among the through-holes 304, the fluid will have a tendency to flow through that hole to the corresponding vertical groove 406 rather than overcoming the fluid resistance by flowing through the remaining narrow spiral conduit 102. The fluid is then stopped at the end of the corresponding vertical groove 406 when the corresponding hole among the flow rate selection holes 408 of the seal liner 400 is blocked by the cylindrical wall 216 of the rotor cap 200. Once the fluid fills in the vertical groove 406 of the seal liner 400, the fluid has no other way to flow other than continuing to flow through the narrow spiral conduit 102. This phenomenon for other communication through-holes 304 and other vertical recesses 406 continues until the fluid comes across the fluid path of the selected flow rate.

Adjusting Flow Rate

In some embodiments, a desired flow rate is selected from the preset flow rates by rotating the rotor cap 200, such that a bottom hole 210 of the cylindrical wall 216 of the rotor cap 200, which communicates with the outlet chamber 206, is aligned with a selected one of the flow rate selection holes 408. This allows the fluid flow of the desired flow rate a into the outlet chamber 206, as shown in FIG. 11.

As discussed above, in order for the flow regulator 50 to provide a flow rate selecting function, in some embodiments, the sleeve 300 contains as many "flow rate selection" through-holes 304 as therapy requires. In the illustrated embodiments, flow rate selection is not continuous, but discrete, which allows a clear step mode in varying the flow rate. A plurality of through-holes 304 of the sleeve 300 can be equally distributed azimuthally around the sleeve 300, but not limited thereto. The number of flow rate variations can be any number determined by the number of through-holes 304 formed in the sleeve 300 and mating vertical passages 406 formed in the seal liner 400. The only limitation is the space to place the through-holes 304 of the sleeve 300 and the vertical passages 406 of the seal liner 400 and the indicating marks outside the device. Each through-hole 304 of the sleeve 300 communicates with a corresponding vertical passage 406 of the seal liner 400, which connects to a corresponding one of the outlet holes 408 formed at the lower portion of the seal liner 400. In one embodiment, only one of the outlet holes 408 of the seal liner 400 is aligned with the bottom hole 210 of the rotor cap 200 to fluidly communicate with the outlet chamber 206 through the bottom hole 210 of the rotor cap 200. All interfacing surfaces between the sleeve 300 and the seal liner 400 other than the through-holes 304, the outlet holes 408 and the vertical passages 406 are sealed by the seal liner 400.

Circumferential Channel

Figure 9:
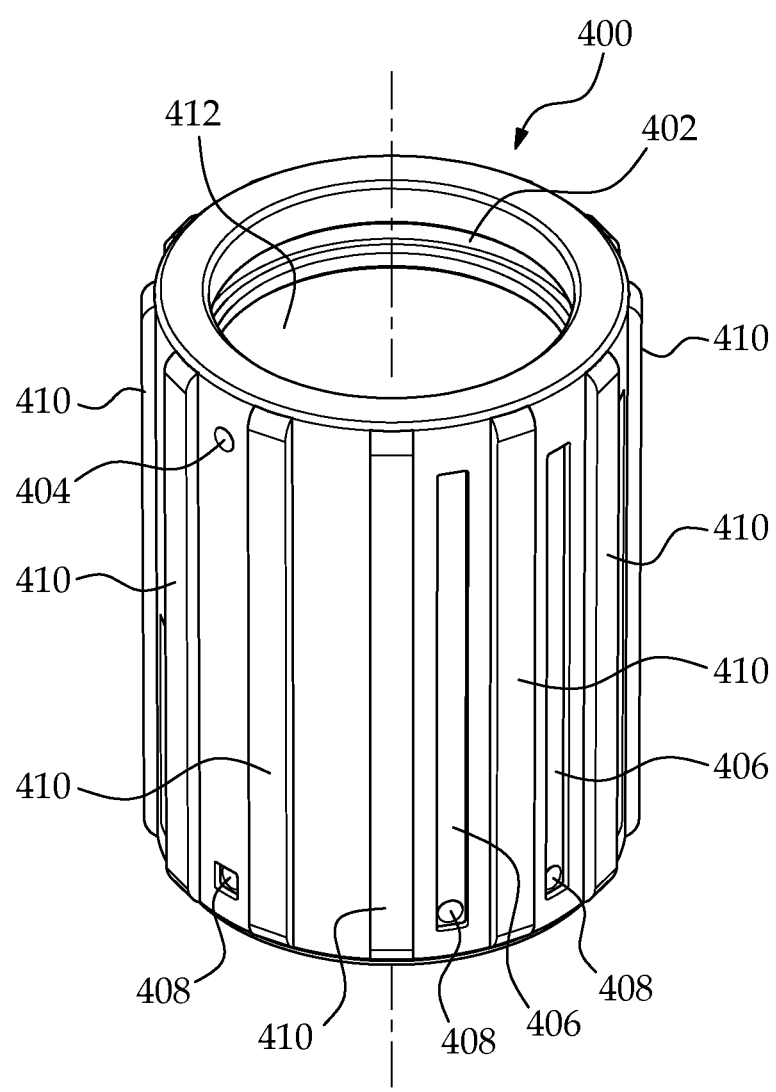
FIG. 9 is a perspective view of a seal liner of the flow regulator in accordance with one embodiment.

Referring to FIGS. 2B and 9, in some embodiments, the seal liner 400 includes a circumferentially extending groove or circumferential channel 402. The circumferential channel 402 communicates with the upper chamber 202 of the rotor cap 200 regardless of the rotational position of the rotor cap 200. In other words, the circumferential channel 402 allows for continuous flow and communication regardless of the position of the rotor cap 200. The circumferential channel 402 extends over the entire circumference of the inner surface of the seal liner 300. As can be seen in the illustrated embodiment, the circumferential channel 402 can be fabricated on the inside wall of the seal liner. In an alternative embodiment, such circumferential channel groove can be formed over the outer surface of the cylindrical wall 216 of the rotor cap 200.

Seal Liner Support

Referring to FIGS. 2B and 3, in some embodiments, the seal liner support 500 is positioned at the indented area 412 of the seal liner 400. The support 500 is made of a thermoplastic like ABS or Polycarbonate, but not limited thereto, so it can provide the necessary mechanical strength to push the seal liner onto the inner wall 310 of the sleeve 300.

In some embodiments, the outside diameter of the seal liner support 500 is larger than the inside diameter of the indented area 412 of the seal liner 400, so it can push the seal liner 400 against the inside wall of the mating sleeve 300, and provide a fluid seal between the seal liner 400 and the sleeve 300. The inner diameter of the seal liner support 500 is larger than the outer diameter of the cylindrical portion 216 of the rotor cap 200, so there is no contact between the two bodies 400 and 216. Contact between the rotor cap 200 and the seal liner 400 occurs only at the un-indented areas (top and bottom) of the seal liner 400 and the cylinder portion 216 of the rotor cap 200.

Rotor Cap

Referring to FIGS. 2A, 2B, 3, 11 and 13A-13C, the rotor cap 200 includes a top wall 218 and an outer wall 220 extending from the top wall 218. Knurls may be provided around the outer wall 220. The outer wall 220 includes a second protrusion 214 on its inner surface which forms a snap-fit-engagement with the first protrusion 114 of the bottom housing 100. The rotor cap 200 is rotatable with respect to the bottom housing 100. The rotor cap 200 further includes a cylinder portion 216 extending from the top wall 218 and extending toward the bottom wall 107 of the bottom housing 100. At the end of the cylindrical wall 216 a seal 222 may optionally be provided. The seal 222 contacts the bottom wall 107 of the bottom housing 100 to provide a fluid seal. The rotor cap 200 has an inlet port 204 which can be connected to a tube 54 extending from the pump 52.

The rotor cap 200 is made of a thermoplastic like polypropylene or polycarbonate, but not limited thereto, so it can provide sufficient rigidity and structural integrity. As discussed above, the rotor cap 200 includes a cylinder portion 216 which provides inlet and outlet chambers 202 and 206, respectively. The rotor cap 200 is able to rotate and allows the selection of different flow rates.

Piston Assembly

Referring to FIGS. 2, 3, 11, 12A, 12B and 13A-13C, in some embodiments, the piston assembly 650 is received inside the cylinder portion 216 of the rotor cap 200 with interference fit, so it can provide a sufficient seal under a certain pressure. The piston assembly 650 can slide up and down the cylindrical wall 216 depending on the pressure changes of the two chambers 202 and 206. The piston assembly 650 includes a piston 600. The central portion of the piston 600 includes a diaphragm 602. The tip of the piston 600 has a cone shape, and the mating valve seat 104 has a concave cone shape as well so as to maximize the seal function. In one embodiment, the diaphragm 602 and the valve seat 104 form an outlet valve 120.

In some embodiments, inside of the piston 600, a rigid plastic piston ring 700 is inserted to support the piston 600 against the cylinder wall 216. Without this ring 700, the piston 600 is likely to collapse or buckle under severe pressure. The ring 700 is mechanically inserted into the mating cavity of the piston 600, and moves with the piston 600 as one body.

Stopper

Referring to FIGS. 2, 3, 11, 12B, and 13A-13C, in embodiments, the stopper 800 is placed in the outlet chamber 206 under the piston 600. The stopper 800 is made of elastomeric tubing. It includes a small cut-out at the bottom so that the fluid can pass freely into the outlet chamber 206 from the bottom hole 210 of the cylinder wall 216. The elastomeric property of the stopper 800 will help adjustment of the resilience along with the spring-back of the diaphragm 602.

In some embodiments, the length of the stopper 800 determines the initial gap between the diaphragm 602 and the valve seat 104 of the bottom housing 100, which determines the equilibrium of the pressure differential and the resilience of the piston 600 and the stopper 800. The length of the stopper 800 can vary depending on the infusion pump 52 to be connected to the flow regulator 50, which exerts different pump pressures. Therefore, the flow regulator 50 can be used for any mechanical type disposable ambulatory pumps by adjusting the length of the stopper 800 for each pump.

The inner diameter and the outer diameter of the stopper 800 are determined by the rigid portion of the piston 600 so that it does not block the flexible part (diaphragm 602). The stopper 800 can minimize the residual amount of the expensive drug in the outlet chamber 206.

Movable Diaphragm

In some embodiments, the diaphragm 602 divides the inlet chamber 202 and the outlet chamber 206. The diaphragm is movable and slides along the inside wall 216 of the rotor cap 200. The diaphragm 602 is part of the piston 600 which can seal the fluid between the inlet chamber 202 and the outlet chamber 206 while being movable along the cylinder wall 216.

In some embodiments, the diaphragm 602 is not fixed to a certain position of the cylinder wall so it does not need any fixation means. Unlike a fixed type diaphragm (which is fixed at a fixed location), the piston 600 (along with the diaphragm 602) moves freely along the cylinder wall 216, which makes the resilience of the diaphragm adjustable. Contrastingly, in the fixed type diaphragm, the initial gap and the resilience of the diaphragm are fixed. Unlike the fixed type diaphragm, the piston 600 is stopped by the stopper 800 in order to determine the initial gap. Depending on the pressure of the pump to be used, one of several stoppers having various lengths can be selected during the manufacture of the flow regulator. Thus, it is easy to adjust the initial gap depending on the pump pressure. Contrastingly, in the fixed type diaphragm, it is difficult to adjust the initial gap, and such adjustment requires changes of dimensions of several components.

Pressure Differential

In some embodiments, the flow regulator concept is based on the pressure differential between the pressures upstream and downstream of the flow restrictor (for example, spiral conduit 102). The flow restrictor is injection-molded as a part of the regulator; hence the illustrated embodiment of the invention does not need a separate flow restrictor, unlike other concepts. A movable diaphragm 602, which slides up and down in the closed fluid chamber, acts as a flow valve to balance the pressure differential.

In some embodiments, when the inlet pressure increases (or the difference between the pressure in the inlet chamber 202 and that in the outlet chamber 206 increases), the resilient elastomeric diaphragm 602 positioned by the stopper 800 deflects, thereby at least partially closing an outlet port 106 and reducing the flow amount. If the inlet pressure decreases and/or the outlet pressure increases (or the difference decreases), the resilient diaphragm 602 relaxes to its original shape, opening the outlet port 106 and allowing increased flow. Some of the critical variables affecting the regulating performance are the initial length of the stopper 800, which determines the distance between the diaphragm 602 and the valve seat 104, dimensions of the flow restrictor (i.e., spiral conduit 102) and the dimension and material property (including resiliency) of the diaphragm 602.

Pressure Regulation

The flow regulator 50 works according to the concept of a constant pressure differential. The flow restrictor (i.e., conduit 102) together with a sliding piston 600 is a part of the flow regulator 50 that acts as a valve to maintain the pressure differential. As discussed above, when the inlet pressure increases (or the difference between the pressure in the inlet chamber 202 and that in the outlet chamber increases), the thinned area 604 of the diaphragm part 602 of the piston 600 deflects, at least partially closing the outlet valve 120 and reducing the fluid flow rate. If the inlet pressure decreases (or the difference decreases), the diaphragm 602 relaxes, opening the outlet valve 120 and allowing increased flow.

Flow Through Outlet Valve

Referring to FIGS. 11, 13A, 13B, and 13C, in some embodiments, when the bottom hole 210 of the rotor cap 200 is aligned to one selected outlet hole 408 of the seal liner for a desired flow rate, the fluid flows into the outlet chamber 206 of the rotor cap cylinder wall 216. The fluid pressure decreases while passing through the narrow, spiral or helical shaped conduit 102, and becomes much lower than the initial pressure of the inlet chamber 202.

Figure 13A:
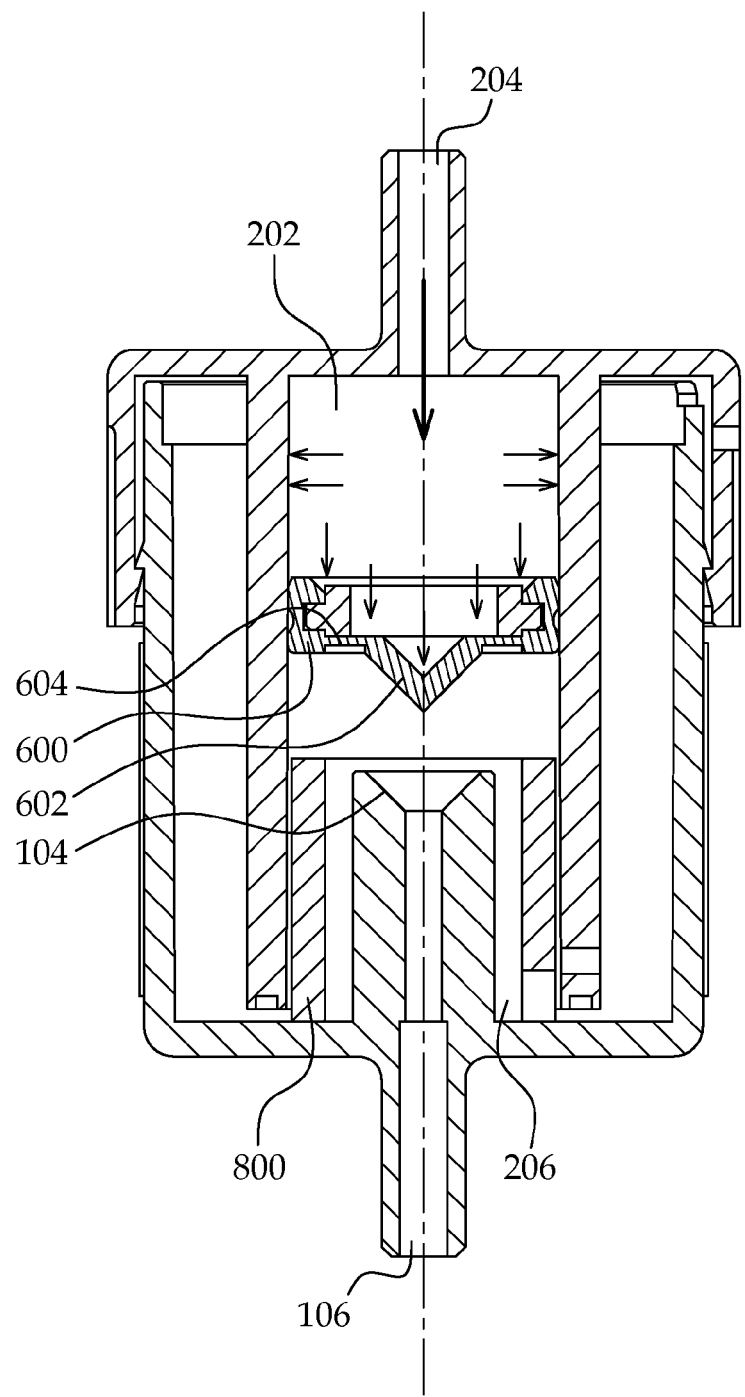
FIGS. 13A, 13B and 13C are sectional views of a rotor cap and a bottom housing of the flow regulator, illustrating the operation of a piston in accordance with one embodiment.

The pressure differential between the two chambers 202 and 206 causes movement of the diaphragm 602 of the piston 600 toward the valve seat 104 with respect to the cylinder wall 216 as shown in FIG. 13A. Once the piston 600 hits the stopper 800, then the thinned area 604 of the diaphragm 602 of the piston 600 starts to deflect downward. This deflection takes place in the elastic region of the piston material (elastomer). This states that when the pressure differential changes, the diaphragm 602 has a tendency to spring back to the original shape. This resilience is determined by the elastomer material, geometry of the diaphragm (thickness and diameter of the thinned area 604), and the initial height difference between the stopper 800 and the central boss 118 of the bottom housing 100.

Figure 13B:
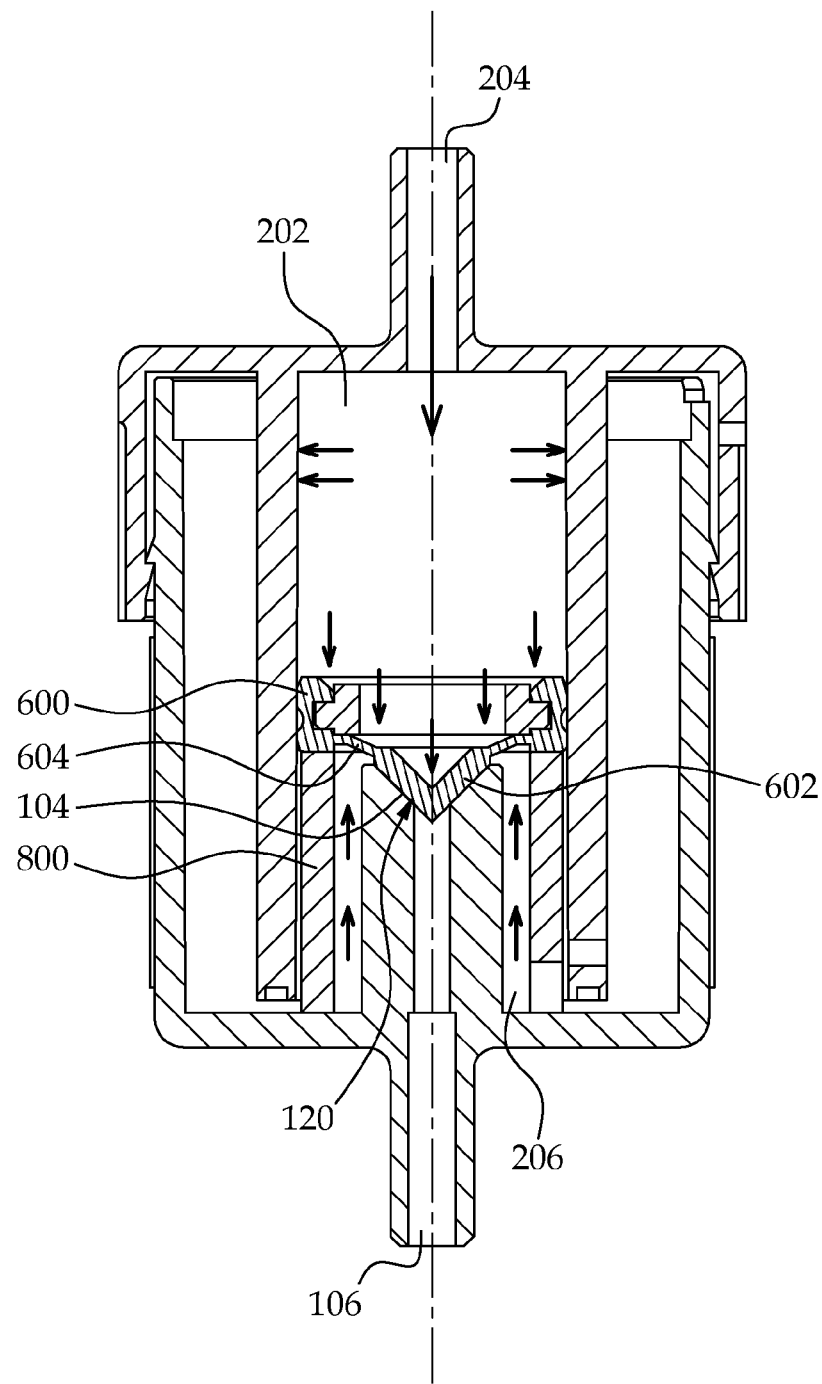

When the diaphragm 602 deflects downward, the conical center piece of the piston 600 starts to contact the valve seat 104, close the outlet valve 120 and stops the flow as shown in FIG. 13B. Even after the fluid stops at the outlet valve 120, fluid continues to flow through the spiral or helical flow restrictor 102 because a pressure differential still exists between the inlet and outlet chambers 202 and 206. As it continues to flow, the pressure differential decreases until it reaches the point where there is no more pressure differential.

Figure 13C:
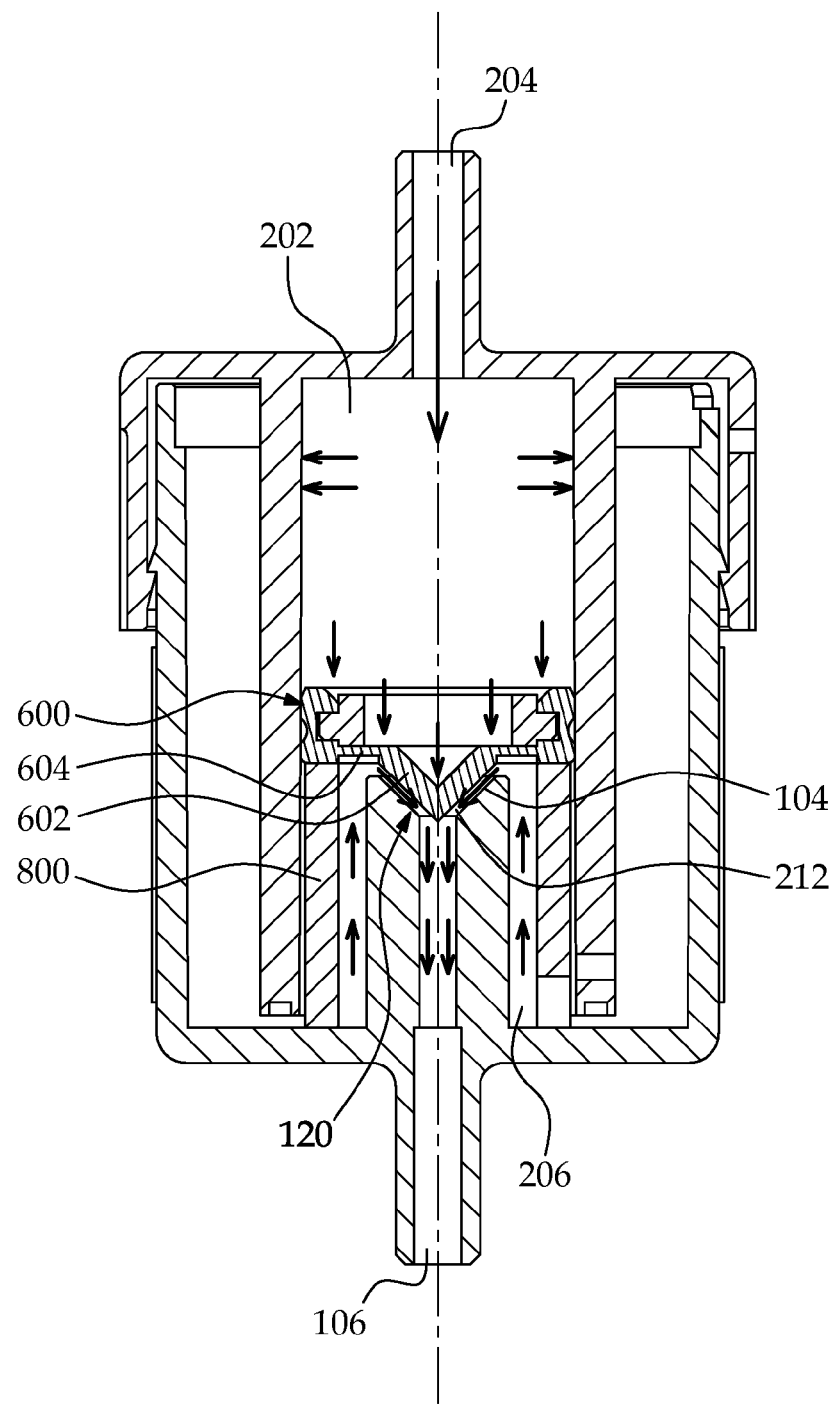

However, in the illustrated embodiments, before it reaches such an equilibrium point, the diaphragm of the piston 600 will begin to push back upward toward the inlet chamber 202 as shown in FIG. 13C, because it lost the pressure which held the diaphragm 602 deflected downward. The fluid starts to flow again, and the pressure in the outlet chamber 206 starts to decrease. Consequently, the pressure differential between the two chambers increases. Then the system repeats the same cycle; the diaphragm 602 deflects and closes the fluid.

Advantages

Flow regulators in accordance with embodiments can have the following advantages:

Consistent flow rate over the entire course of infusion regardless of the upstream pressure variation.

Flow rates which can be as little as 0.5 mL/hr by utilizing precision injection molding technology.

A small size which is smaller than or at least the same as the typical flow rate varying units currently available in the market.

Manufacturing costs which are lower than typical flow rate varying units currently available in the market.

Users can benefit from improved accuracy, and more flow rate variation options with no extra cost simply by replacing typical units currently available in the market with the flow regulator according to the embodiments.

Minimization of the effect of head height, partial fill, and down-stream resistance resulting from different access points or the use of different types of catheters.

Adjustability to different pressure sources (different pumps).

Reduction in the number of no-flow failures due to capillary air blockage. Provision of a closed, in-line filtration system to meet regulatory standards.

Reduction in the variability of medication delivery times under standard conditions through the elimination of the effect of balloon pressure variability.

Development of a miniaturized, body conforming device to maximize patient comfort and operating temperature stability.

More flexibility of dosage which allows more precise prescriptions based on the patient's needs.

Prevention of the unnecessary overuse of narcotic drugs.

No individual adjustment is required.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A drug infusion flow regulating apparatus comprising:
an inlet configured to receive liquid into the apparatus;
an outlet configured to discharge the liquid from the apparatus;
a cylinder assembly comprising a first cylinder, a second cylinder and a third cylinder that are arranged along an axial direction;
the first cylinder comprising a first interior surface;
a continuous helical thread formed into the first interior surface of the first cylinder;
the second cylinder fitted into the first cylinder and comprising a second interior surface and a second exterior surface;
a helical liquid-flow channel formed between the first cylinder and the second cylinder through the continuous helical thread, the helical liquid-flow channel being in fluid communication with the inlet;
a plurality of longitudinal grooves extending along the axial direction and formed into the second cylinder on the side of the second interior surface;
a plurality of through-holes formed in the second cylinder and in fluid communication with the helical liquid-flow channel;
the third cylinder fitted into the second cylinder and comprising a third exterior surface;
a plurality of independent liquid-flow passages formed between the second cylinder and the third cylinder, wherein each of the plurality of independent liquid-flow passages is in fluid communication with the helical liquid-flow channel via at least one of the plurality of through-holes; and
a diaphragm valve configured to regulate fluid communication between the helical liquid-flow channel and the outlet.

2. The apparatus of claim 1, wherein two immediately neighboring liquid-flow passages are liquid-tightly separated from each other by close contact between the second interior surface and the third exterior surface.

3. The apparatus of claim 2, wherein the apparatus is configured such that at least one of the plurality of passages is selected to form a fluid channel extending to the diaphragm valve while the other passages do not form a fluid channel extending to the diaphragm valve.

4. The apparatus of claim 2, further comprising a fourth cylinder received within the third cylinder and rotatable relative to the third cylinder,
wherein at least one of the plurality of passages forms a fluid channel extending to the diaphragm valve depending upon a rotational position of the fourth cylinder relative to the third cylinder.

5. The apparatus of claim 4, wherein the diaphragm valve comprises a deformable diaphragm and a valve seat that are received in an interior space of the fourth cylinder,
wherein the deformable diaphragm divides the interior space into a first chamber and a second chamber, wherein the inlet is fluidly connected to the first chamber, and the outlet is fluidly connected to the second chamber,
wherein the diaphragm is configured to deform toward the valve seat and recover away from the valve seat in response to the pressure differential between the first and second chambers.

6. The apparatus of claim 5, wherein the deformable diaphragm is slidable within the fourth cylinder such that the size of the first and second chambers varies.

7. The apparatus of claim 6, further comprising a stopper configured to stop the movement of the diaphragm at a predetermined location.

8. The apparatus of claim 1, wherein the plurality of through holes are angularly separated along the second cylinder's circumference.

9. The apparatus of claim 1, wherein the plurality of independent liquid-flow passages are angularly separated along the third cylinder's circumference.

10. The apparatus of claim 1, wherein one or more of the plurality of independent liquid-flow passages have a liquid-flow passage portion extending along the axial direction.

11. The apparatus of claim 1, wherein the first cylinder is made of a first material, the second cylinder is made of a second material and the third cylinder is made of a third material, wherein the first material is harder than the second material and the second material is harder than the third material.

12. The apparatus of claim 1, wherein the second cylinder is made of a non-elastomeric material having a modulus of elasticity greater than 2,000 psi.

13. The apparatus of claim 1, wherein the third cylinder is made of an elastomeric material having a modulus of elasticity smaller than 1,000 psi.

14. The apparatus of claim 1, wherein each of the plurality of longitudinal grooves extends throughout the length of the second cylinder.

15. The apparatus of claim 1, wherein the plurality of through-holes are located at different positions in the axial direction.

16. The apparatus of claim 1, wherein two immediately neighboring passages are liquid-tightly separated by liquid-tight fitting of the third cylinder into the second cylinder.

17. The apparatus of claim 1, further comprising a fifth cylinder fitted into the third cylinder and located between the third cylinder and fourth cylinder.

18. A method of making the apparatus of claim 1, the method comprising: providing the apparatus of claim 1, wherein provision of the apparatus comprises: providing
the first cylinder made of a first material and comprising the continuous helical thread formed into the first interior surface, the first cylinder having a first diameter measured on the first interior surface;
providing the second cylinder made of a second material softer than the first material, the second cylinder having a second diameter on the second exterior surface, wherein the second diameter is greater than the first diameter; and
press-fitting the second cylinder into the first cylinder,
wherein the second material is a non-elastomer having a modulus of elasticity greater than 2,000 psi.

19. The method of claim 18, wherein press-fitting of the second cylinder into the first cylinder causes deformation of the second cylinder along the plurality of grooves such that the second diameter shrinks.

20. The method of claim 18, further comprising:
providing the third cylinder made of a third material that is an elastomer having a modulus of elasticity smaller than 1,000 psi, wherein the third cylinder comprises a plurality of longitudinal ribs protruding from the third exterior surface; and
press-fitting the third cylinder into the second cylinder such that two immediately neighboring passages are liquid-tightly separated by press-fitting of the third cylinder into the second cylinder.

21. The apparatus of claim 1, wherein the first cylinder, the second cylinder and the third cylinder are arranged along the axial direction in a coaxial manner.

* * * * *